United States Patent
Sgroi

(10) Patent No.: US 10,376,401 B2
(45) Date of Patent: *Aug. 13, 2019

(54) REINFORCEMENT SCAFFOLDS FOR MAINTAINING A REDUCED SIZE OF A STOMACH AND METHODS OF USE

(71) Applicant: Covidien LP, Mansfield, MA (US)

(72) Inventor: Anthony Sgroi, Wallingford, CT (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/056,594

(22) Filed: Aug. 7, 2018

(65) Prior Publication Data

US 2018/0338850 A1    Nov. 29, 2018

Related U.S. Application Data

(63) Continuation of application No. 15/066,684, filed on Mar. 10, 2016, now Pat. No. 10,039,662.

(60) Provisional application No. 62/150,938, filed on Apr. 22, 2015.

(51) Int. Cl.
*A61F 13/00* (2006.01)
*A61F 5/00* (2006.01)

(52) U.S. Cl.
CPC .......... *A61F 5/0086* (2013.01); *A61F 5/0076* (2013.01); *A61F 5/0089* (2013.01)

(58) Field of Classification Search
CPC .... A61F 5/0013; A61F 5/0063; A61F 5/0076; A61F 5/0083; A61F 5/008; A61F 5/00896

USPC .......................................................... 600/37
See application file for complete search history.

(56) References Cited

U.S. PATENT DOCUMENTS

| | | |
|---|---|---|
| 3,227,154 A | 1/1966 | Cook |
| 4,328,805 A | 5/1982 | Akopov et al. |
| 4,403,604 A | 9/1983 | Wilkinson et al. |
| 5,246,456 A | 9/1993 | Wilkinson |
| 5,297,536 A | 3/1994 | Wilk |
| 5,382,231 A | 1/1995 | Shlain |
| 5,401,241 A | 3/1995 | Delany |
| 5,458,131 A | 10/1995 | Wilk |
| 5,465,709 A | 11/1995 | Dickie et al. |

(Continued)

FOREIGN PATENT DOCUMENTS

| | | |
|---|---|---|
| CN | 201365906 Y | 12/2009 |
| CN | 102626536 A | 8/2012 |

(Continued)

OTHER PUBLICATIONS

International Search Report and Written Opinion of hte International Searching Authoirity, dated Jul. 12, 2016, corresponding to International ApplicationNo. PCT/US2016/028046; 12 total pages.

(Continued)

*Primary Examiner* — John P Lacyk

(57) ABSTRACT

A method of performing bariatric surgery includes inserting a gastrectomy device into a stomach of a patient, positioning the gastrectomy device in a selected location in the stomach, transecting a portion of the stomach thereby reducing a size of the stomach, and applying a reinforcement scaffold to an outer surface of the stomach. The reinforcement scaffold is configured to maintain the reduced size of the stomach.

11 Claims, 4 Drawing Sheets

(56) References Cited

U.S. PATENT DOCUMENTS

| | | | |
|---|---|---|---|
| 5,718,666 | A | 2/1998 | Alarcon |
| 7,153,131 | B2 | 12/2006 | Crohn |
| 8,092,378 | B2 | 1/2012 | Roth et al. |
| 8,147,502 | B2 | 4/2012 | Albrecht et al. |
| 8,192,448 | B2 | 6/2012 | Bessler et al. |
| 8,454,503 | B2 | 6/2013 | Roth et al. |
| 8,663,149 | B2 | 3/2014 | Gagner et al. |
| 10,039,662 | B2 * | 8/2018 | Sgroi ............. A61F 5/0086 |
| 2002/0091395 | A1 | 7/2002 | Gabbay |
| 2004/0006351 | A1 | 1/2004 | Gannoe et al. |
| 2004/0092974 | A1 | 5/2004 | Gannoe et al. |
| 2005/0119674 | A1 | 6/2005 | Gingras |
| 2005/0203489 | A1 | 9/2005 | Saadat et al. |
| 2005/0251158 | A1 | 11/2005 | Saadat et al. |
| 2006/0200004 | A1 | 9/2006 | Wilk |
| 2006/0241344 | A1 | 10/2006 | Wilk |
| 2006/0241570 | A1 | 10/2006 | Wilk |
| 2007/0032702 | A1 | 2/2007 | Ortiz |
| 2009/0276055 | A1 | 11/2009 | Harris et al. |
| 2010/0179417 | A1 | 7/2010 | Russo |
| 2011/0178454 | A1 | 7/2011 | Gagner et al. |
| 2011/0288576 | A1 | 11/2011 | Hoffman |
| 2012/0065469 | A1 | 3/2012 | Allyn et al. |
| 2012/0165608 | A1 | 6/2012 | Banik et al. |
| 2012/0184981 | A1 | 7/2012 | Pecor et al. |
| 2012/0239061 | A1 | 9/2012 | Mathur |
| 2013/0165774 | A1 | 6/2013 | Nocca |
| 2014/0018722 | A1 | 1/2014 | Scott et al. |
| 2014/0114121 | A1 | 4/2014 | Trivedi |
| 2014/0179989 | A1 | 6/2014 | Gingras |

FOREIGN PATENT DOCUMENTS

| | | | |
|---|---|---|---|
| EP | 2246013 | A1 | 11/2010 |
| ES | 2326937 | A1 | 10/2009 |
| JP | 3178309 | U | 9/2012 |
| WO | 02096327 | A2 | 12/2002 |
| WO | 2009097585 | A1 | 8/2009 |
| WO | 2012138737 | A1 | 10/2012 |
| WO | 2013123235 | A1 | 8/2013 |
| WO | 2014062881 | A1 | 4/2014 |
| WO | 2015052720 | A1 | 4/2015 |

OTHER PUBLICATIONS

European Search Report dated Oct. 4, 2016, corresponding to European Application No. 16178267.7; 7 pages.

European Communication dated May 26, 2017, corresponding to European Application No. 15167342.3; 4 pages.

European Search Report, dated Mar. 24, 2017, corresponding to European Application No. 16199748.1; 5 pages.

European Search Report, dated Mar. 19, 2015, corresponding to European Application No. 14192226.0; 7 pages.

European Search Report, dated Mar. 24, 2015, corresponding to European Application No. 14192416.7; 7 pages.

Dietel et al., "Endoscopy of Vertical Banded Gastroplasty," The American Surgeon, May 1989, vol. 55; pp. 287-890.

Dietel et al., "Vertical Banded Gastroplasty: Results in 233 Patients," The Canadian Journal of Surgery, Sep. 1986, vol. 29, No. 5; pp. 322-324.

Mason et al., "Vertical Gastroplasty: Evolution of Vertical Banded Gastroplasty,"World Journal of Surgery, Sep. 1998, vol. 22, No. 9; pp. 919-924.

Extended European Search Report dated Sep. 17, 2015, corresponding to European Patent Application 15167339.9; 10 pages.

Extended European Search Report dated Oct. 1, 2015, corresponding to European Application No. 15167342.3; 7 pages.

European Search Report dated Dec. 2, 2015, corresponding to European Application No. 151772332; 7 pages.

European Search Report dated Mar. 26, 2019, corresponding to counterpart corresponding European Application No. 16783639A; 7 pages.

* cited by examiner

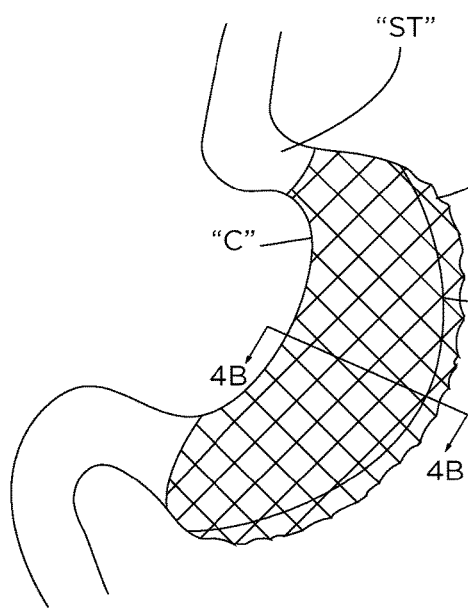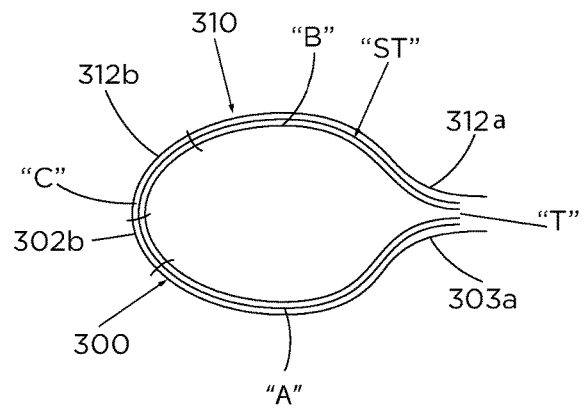
FIG. 4A
FIG. 4B

REINFORCEMENT SCAFFOLDS FOR MAINTAINING A REDUCED SIZE OF A STOMACH AND METHODS OF USE

CROSS-REFERENCE TO RELATED APPLICATIONS

This patent application is a continuation application of U.S. patent application Ser. No. 15/066,684, filed on Mar. 10, 2016 (now U.S. Pat. No. 10,039,662), which the claims the benefit of and priority to U.S. Provisional Patent Application No. 62/150,938, filed on Apr. 22, 2015, the entire contents of each of which being incorporated by reference herein.

TECHNICAL FIELD

The present disclosure generally relates to surgical systems, and more particularly, to surgical systems used in bariatric procedures and methods of performing bariatric procedures.

BACKGROUND

Obesity is reaching epidemic proportions in many regions of the world, particularly in the United States. In order to treat obesity, various bariatric procedures have been developed including, for example, gastric bypass, adjustable gastric banding, and sleeve gastrectomy. The goal in each of these procedures is to reduce the stomach capacity to restrict the amount of food that the patient can eat. The reduced stomach capacity, in turn, results in a feeling of fullness for the patient after ingesting a relatively smaller amount of food. Thus, the patient can achieve significant weight loss.

Sleeve gastrectomy involves transecting a stomach, e.g., using a stapling device or other suitable device, to reduce a stomach volume. Sleeve gastrectomy procedures are often aided by the use of a gastrectomy device, which serves as a guide or template for transecting the stomach to the appropriate configuration while inhibiting inadvertent transection of stomach or esophageal tissue. Once the stomach has been appropriately transected, the gastrectomy device is removed and a leak test is performed to determine whether there are any areas of extravasation.

In some circumstances, a patient post-surgery may intake meals that are larger than recommended, which subjects the reduced size stomach to mechanical stretching. If the patient continues to intake larger meals, the reduced size stomach may begin to assume an enlarged size approximating the pre-surgery stomach size, thus at least partially negating the benefits sought by the sleeve gastrectomy procedure.

Accordingly, it may be desirable to provide a way to aid in maintaining the reduced size of the stomach post-surgery to counteract excessive eating by a patient.

SUMMARY

According to one aspect of the present disclosure, a method of performing bariatric surgery is provided. The method includes inserting a gastrectomy device into a stomach of a patient, positioning the gastrectomy device in a selected location in the stomach, transecting a portion of the stomach thereby reducing a size of the stomach, and applying a reinforcement scaffold to an outer surface of the stomach. The reinforcement scaffold is configured to maintain the reduced size of the stomach.

In some embodiments, applying the reinforcement scaffold may include wrapping the reinforcement scaffold about the outer surface of the stomach to conform the reinforcement scaffold to the outer surface of the stomach.

It is contemplated that applying the reinforcement scaffold may include attaching a first end of the reinforcement scaffold to a portion of the stomach and attaching a second end of the reinforcement scaffold to the portion of the stomach to form a sleeve around the stomach that has a diameter approximating a diameter of the stomach.

It is envisioned that applying the reinforcement scaffold may include applying a first reinforcement scaffold to a first longitudinal section of the stomach, and applying a second reinforcement scaffold to a second longitudinal section of the stomach.

In some aspects, applying the reinforcement scaffold may include suturing, gluing, or stapling the reinforcement scaffold to the stomach.

In some embodiments, the reinforcement scaffold may be fabricated from a material that substantially resists expansion.

It is contemplated that transecting the portion of the stomach may include stapling the portion of the stomach.

It is envisioned that applying the reinforcement scaffold may include attaching a first end of the reinforcement scaffold to a transection line formed in the stomach.

In some aspects, reducing the size of the stomach may include forming the stomach into a tubular configuration.

In another aspect of the present disclosure, a system for use in a bariatric surgical procedure is provided. The system includes a sleeve gastrectomy device and a reinforcement scaffold. The gastrectomy device has a proximal end and a distal end and defines a channel therebetween. The proximal end defines an opening therein configured to be coupled with a vacuum source. The distal end has a blunt tip. The gastrectomy device has a series of openings defined along its length in communication with the channel. The reinforcement scaffold is configured to enshroud a stomach having a reduced size to maintain the reduced size of the stomach.

In some embodiments, the reinforcement scaffold may be fabricated from a material that substantially resists expansion.

It is contemplated that the reinforcement scaffold may include a first reinforcement scaffold sized to enshroud a first longitudinal section of the reduced size stomach, and a second reinforcement scaffold sized to enshroud a second longitudinal section of the reduced size stomach.

It is envisioned that the reinforcement material may be selected from the group consisting of a mesh and a buttress.

In some embodiments, a plurality of reinforcement scaffolds may be provided.

Other aspects, features, and advantages of the present disclosure will be apparent from the description, the drawings, and the claims.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein:

FIG. 4A is a perspective view of a pair of reinforcement scaffolds wrapped about a portion of a stomach after a sleeve gastrectomy procedure; and FIG. 4B is an end cross-sectional view, taken along line 4B-4B of FIG. 4A, of the reinforcement scaffolds wrapped around the stomach.

DETAILED DESCRIPTION

As used herein, the term "clinician" refers to a doctor, nurse, or other care provider and may include support personnel. The terms "proximal" or "trailing" each refer to the portion of a structure closer to a clinician, and the terms "distal" or "leading" each refer to a portion of a structure farther from the clinician.

Figure 1:
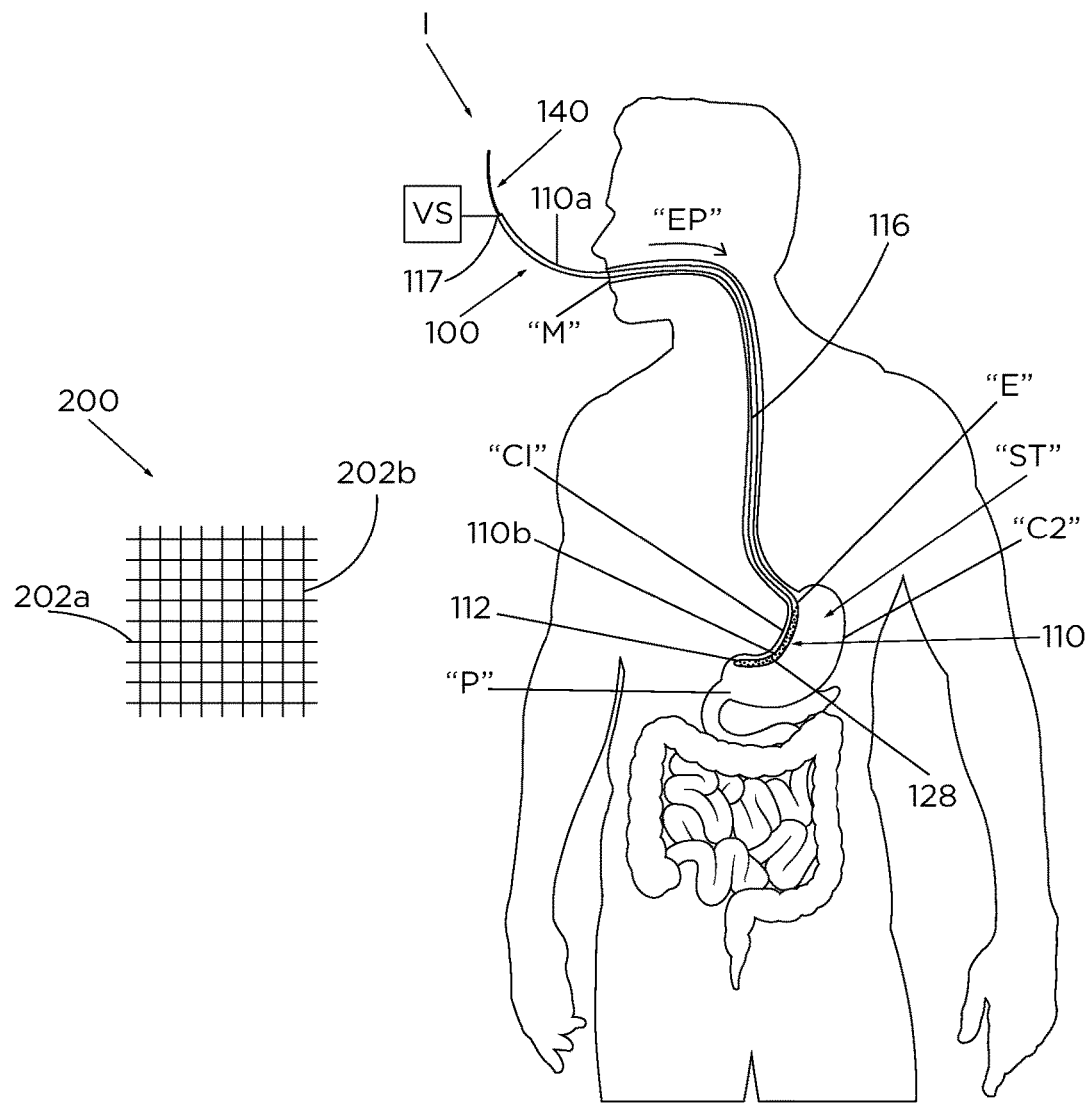
FIG. 1 is a front view of an illustrative embodiment of a surgical system including a reinforcement scaffold, and a gastrectomy device being navigated through an enteral pathway of a patient into a stomach of a patient in accordance with the principles of the present disclosure.

With reference to FIG. 1, a system 1 for performing bariatric procedures is provided and generally includes a gastrectomy device 100 for reducing a size of a patient's stomach, and a reinforcement scaffold 200 (see also FIG. 3A) to maintain or substantially maintain the reduced size of the patient's stomach. Gastrectomy device 100 includes an elongate tube 110 and a movable component, such as, for example, a sail member 140 supported on or within elongate tube 110. In use, as described in further detail below, gastrectomy device 100 is inserted into an oral cavity (e.g., a mouth "M") of a patient and is advanced distally (i.e., caudally) along an enteral pathway "EP" that includes a track that extends between oral cavity "M" and a stomach "ST" of the patient. Gastrectomy device 100 is positioned in a selected location within the stomach "ST" and a portion of the stomach "ST" is transected to reduce the size of the stomach "ST." After the stomach "ST" is reduced in size, reinforcement scaffold 200 (FIG. 3A) is applied to stomach "ST" to maintain the reduced size of the patient's stomach "ST," as will be described in detail below.

With continued reference to FIG. 1, elongate tube 110 of gastrectomy device 100 can be formed of any material with sufficient flexibility to enable elongate tube 110 to maneuver along the patient's track or enteral pathway "EP" between the oral cavity "M" and the stomach "ST." Elongate tube 110 includes a trailing end or proximal end 110a and a leading end or distal end 110b. Elongate tube 110 extends between the proximal and distal ends 110a, 110b. It is contemplated that elongate tube 110 can be curved along its length, linear, or any shape suitable for a particular bariatric surgical procedure. Elongate tube 110 defines a channel 116 extending along and through the length of elongate tube 110. Elongate tube 110 further includes a series of openings or apertures 128 extending between an outer surface and an inner surface of elongate tube 110. Apertures 128 provide for fluid communication between channel 116 and an environment exterior to elongate tube 110. When suction is applied to elongate tube 110 from a vacuum source "VS," elongate tube 110 can adhere to tissue, such as, for example, stomach tissue, due to the plurality of openings 128 directing suction towards stomach tissue.

Proximal end portion 110a of elongate tube 110 has an opening 117 configured for connection with vacuum source "VS." Distal end 110b of elongate tube includes a distal tip 112. Distal tip 112 has a blunt, arcuate outer surface such that advancement of elongate tube 110 through internal body cavities of a patient allows the elongate tube 110 to follow the track of the body cavities while inhibiting penetration by the distal tip 112 (i.e., distal tip 112 is configured for atraumatic insertion). In some embodiments, distal tip 112 can be variously configured, such as, for example, oval, oblong, tapered, uniform, non-uniform, smooth, polished, and/or rounded.

Sail member 140 of gastrectomy device 100 is formed from a semi-rigid, resiliently flexible material, e.g., a suitable elastomer, and may be in the form of a rod. Sail member 140 defines a length greater than the length of elongate tube 110 such that sail member 140 can be accessed outside the patient and/or remotely of the surgical site. Sail member 140 is supported on elongate tube 110. Distal movement of sail member 140 causes a distal portion of sail member 140 to expand or bow outwardly relative to elongate tube 110.

Further details regarding gastrectomy device 100 and alternate embodiments thereof can be found in U.S. Pat. No. 9,801,748, filed on Oct. 23, 2014, U.S. Pat. No. 9,414,947, filed on May 13, 2014, and U.S. patent application Ser. No. 14/276,269, filed on May 13, 2014 (now U.S. Patent Application Publication No. 2015/0328031, the entire contents of each of which being incorporated by reference herein.

Figures 3A, 3B:
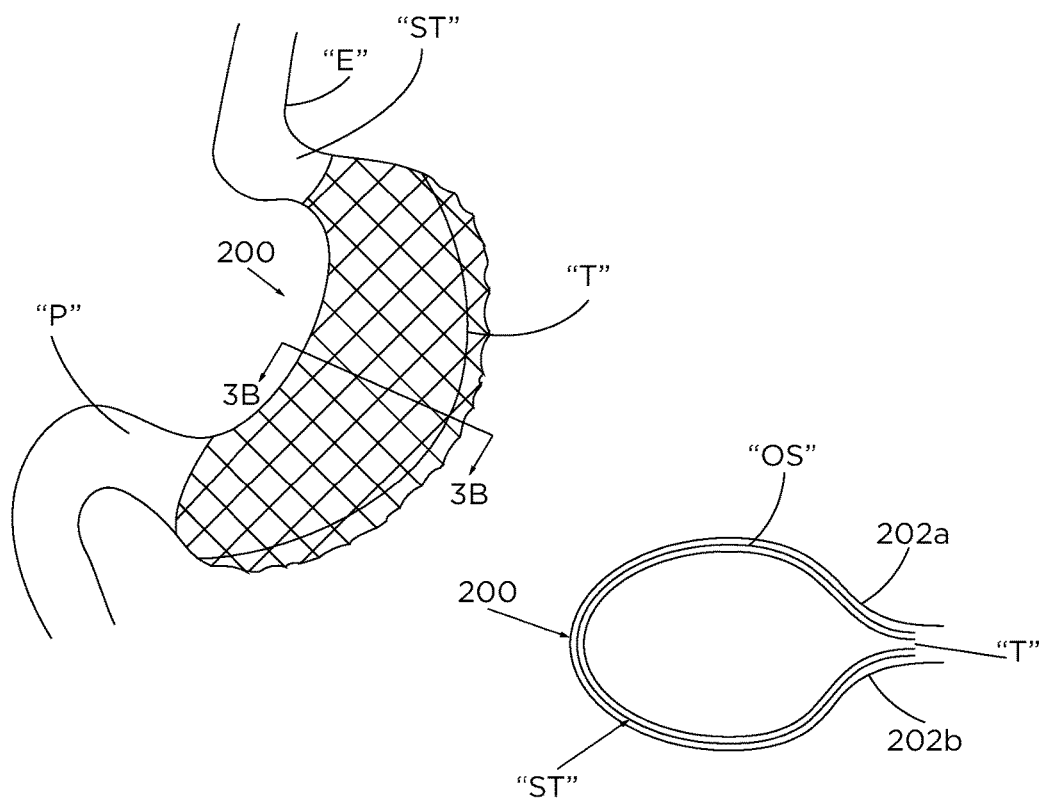
FIG. 3A is a perspective view of the reinforcement scaffold of FIG. 1 wrapped about a portion of a stomach after a sleeve gastrectomy procedure.
FIG. 3B is an end cross-sectional view, taken along line 3B-2B of FIG. 3A, of the reinforcement scaffold wrapped around the stomach.

With reference to FIGS. 3A and 3B, as mentioned above, in addition to gastrectomy device 100, system 1 further includes a reinforcement scaffold 200 used to maintain a reduced size of a stomach, as will be described in detail below. Reinforcement scaffold 200 may be in the form of a surgical buttress, a mesh, or the like, and fabricated from a material that substantially resists stretching/expanding under applied tension. Reinforcement scaffold 200 may be made from any suitable biocompatible natural or synthetic material. The material from which reinforcement scaffold 200 is formed may be bioabsorbable or non-bioabsorbable. It should of course be understood that any combination of natural, synthetic, bioabsorbable, and non-bioabsorbable materials may be used to form reinforcement scaffold 200.

Some non-limiting examples of materials from which reinforcement scaffold 200 may be made include, but are not limited to, metals, poly(lactic acid), poly (glycolic acid), poly (hydroxybutyrate), poly (phosphazine), polyesters, polyethylene glycols, polyethylene oxides, polyacrylamides, polyhydroxyethylmethylacrylate, polyvinylpyrrolidone, polyvinyl alcohols, polyacrylic acid, polyacetate, polycaprolactone, polypropylene, aliphatic polyesters, glycerols, poly (amino acids), copoly (ether-esters), polyalkylene oxalates, polyamides, poly (iminocarbonates), polyalkylene oxalates, polyoxaesters, polyorthoesters, polyphosphazenes and copolymers, block copolymers, homopolymers, blends and combinations thereof.

In embodiments, natural biological polymers may be used in forming reinforcement scaffold 200. Suitable natural biological polymers include, but are not limited to, collagen, gelatin, fibrin, fibrinogen, elastin, keratin, albumin, hydroxyethyl cellulose, cellulose, hydroxypropyl cellulose, carboxyethyl cellulose, chitan, chitosan, and combinations thereof. In addition, the natural biological polymers may be combined with any of the other polymeric materials described herein to produce reinforcement scaffold 200.

Reinforcement scaffold 200 may be porous or non-porous, or combinations of porous and non-porous layers. Where reinforcement scaffold 200 is non-porous, reinforcement scaffold 200 may retard or prevent tissue ingrowth from surrounding tissues thereby acting as an adhesion barrier and preventing the formation of unwanted scar tissue. Thus, in embodiments, reinforcement scaffold 200 possesses anti-adhesion properties. Techniques for forming non-porous layers from such materials are within the purview of those skilled in the art and include, for example, casting, molding, and the like.

In embodiments, reinforcement scaffold 200 is porous and possesses hemostatic properties. Where reinforcement scaffold 200 is porous, it has openings or pores over at least a portion of a surface thereof. Suitable materials for forming the porous layer include, but are not limited to foams (e.g., open or closed cell foams). In embodiments, the pores may be in sufficient number and size so as to interconnect across the entire thickness of the porous layer. In other embodiments, the pores do not interconnect across the entire thickness of the porous layer. In yet other embodiments, the pores do not extend across the entire thickness of the porous layer, but rather are present at a portion of the surface thereof. In embodiments, the openings or pores are located on a portion of the surface of the porous layer, with other portions of the porous layer having a non-porous texture. Those skilled in the art reading the present disclosure will envision other pore distribution patterns and configurations for the porous layer.

Where reinforcement scaffold 200 is porous, the pores may be formed using any method suitable to forming a foam or sponge including, but not limited to the lyophilization or freeze-drying of a composition. Suitable techniques for making foams are within the purview of those skilled in the art. Porous reinforcement scaffold 200 can be at least 0.2 cm thick and is contemplated to be within a range of from about 0.3 to about 1.5 cm thick. Porous reinforcement scaffold 200 can have a density of not more than about 75 mg/cm$^2$ and, in embodiments below about 20 mg/cm$^2$. The size of the pores in the porous reinforcement scaffold 200 can be from about 20 µm to about 300 µm, in embodiments from about 100 µm to about 200 µm.

Reinforcement scaffold 200 may also include a reinforcement member (not explicitly shown). The reinforcement member may be associated with a porous or non-porous layer or may be positioned between a non-porous layer and a porous layer of reinforcement scaffold 200. Alternately, the reinforcement member may be positioned entirely within one or more of the individual layers (i.e., embedded within the porous layer, the non-porous layer, or both) of reinforcement scaffold 200. It is also envisioned that the reinforcement member may be positioned at the surface of one of the layers making up reinforcement scaffold 200 and, in embodiments, may be positioned at an exterior surface of reinforcement scaffold 200.

Some suitable non-limiting examples of reinforcement members include fabrics, meshes, monofilaments, multifilament braids, chopped fibers (sometimes referred to in the art as staple fibers) and combinations thereof. Where the reinforcement member is a mesh, it may be prepared using any technique known to those skilled in the art, such as knitting, weaving, tatting, knipling or the like. Where monofilaments or multifilament braids are used as the reinforcement member, the monofilaments or multifilament braids may be oriented in any desired manner. For example, the monofilaments or multifilament braids may be randomly positioned with respect to each other within reinforcement scaffold 200. As another example, the monofilaments or multifilament braids may be oriented in a common direction within reinforcement scaffold 200. Where chopped fibers are used as the reinforcement member, the chopped fibers may be oriented in any desired manner. For example, the chopped fibers may be randomly oriented or may be oriented in a common direction. The chopped fibers can thus form a non-woven material, such as a mat or a felt. The chopped fibers may be of any suitable length. For example, the chopped may be from 0.1 mm to 100 mm in length, in embodiments, 0.4 mm to 50 mm in length.

It is envisioned that the reinforcement member of reinforcement scaffold 200 may be formed from any bioabsorbable, non-bioabsorbable, natural, or synthetic material previously described herein and combinations thereof. Where monofilaments or multifilament braids are used as the reinforcement member, any commercially available suture material may advantageously be employed as the reinforcement member.

In embodiments, at least one bioactive agent may be combined with reinforcement scaffold 200 and/or any of the individual components (the porous layer, the non-porous layer and/or the reinforcement member) used to construct reinforcement scaffold 200. In these embodiments, reinforcement scaffold 200 can also serve as a vehicle for delivery of the bioactive agent. The term "bioactive agent," as used herein, is used in its broadest sense and includes any substance or mixture of substances that have clinical use, for example, biocidal agents, antimicrobial agents, antibiotics, anti-proliferatives, medicaments, growth factors, anti-clotting agents, clotting agents, analgesics, anesthetics, anti-inflammatory agents, wound repair agents, chemotherapeutics, biologics, protein therapeutics, monoclonal and polyclonal antibodies, DNA, RNA, peptides, polysaccharides, lectins, lipids, probiotics, diagnostic agents, angiogenics, anti-angiogenic drugs, polymeric drugs, and combinations thereof.

With reference to FIG. 1, in operation, gastrectomy device 100 is inserted into a patient, such as, for example, an oral cavity "M" of a patient and is distally advanced toward a stomach "ST" of the patient along an enteral pathway "EP" that extends from the oral cavity "M," through an esophagus of the patient, and into the stomach "ST." Gastrectomy device 100 is further guided through the esophagus and positioned in a selected location in the stomach "ST" of the patient.

Upon positioning gastrectomy device 100 within the selected location in the stomach "ST," sail member 140 is translated distally to bow outwardly relative to elongate tube 110 towards the expanded position (not shown). As sail member 140 bows outwardly towards the expanded position, elongate tube 110 is urged towards and into complementary mating relation with a lesser curvature portion "C1" of the stomach "ST," while sail member 140 is urged towards and into complementary mating relation with a greater curvature portion "C2" of the stomach "ST." As such, the orientation of gastrectomy device 100 with elongate tube 110 extending along the lesser curvature portion "C1" of the stomach "ST" between the esophageal sphincter "E" and the pyloric sphincter "P can be readily achieved. As a result of this configuration of gastrectomy device 100 in the expanded position, the above-described orientation of gastrectomy device 100 within the stomach "ST" is maintained despite spasms, folding, spiraling, and/or shifting of the stomach "ST."

Once the proper orientation of gastrectomy device 100 has been achieved, suction is applied, by vacuum source "VS," within channel 116 for suctioning any remaining contents within the stomach "ST" into channel 116 of elongate tube 110 through apertures 128. Application of suction within channel 116 also suctions the lesser curvature portion "C1" of the stomach "ST" to outer surface or periphery of elongate tube 110, to ensure and maintain the complementary mating relation of elongate tube 110 with the lesser curvature portion "C1" of the stomach "ST."

With elongate tube 110 maintained in position relative to the lesser curvature portion "C1" of the stomach "ST" as a result of the applied suction, sail member 140 may be translated proximally relative to elongate tube 110 such that sail member 140 is pulled inwardly relative to elongate tube 110. As suction is maintained at this point, elongate tube 110 is maintained in the position detailed above despite contraction of sail member 140.

Figure 2:
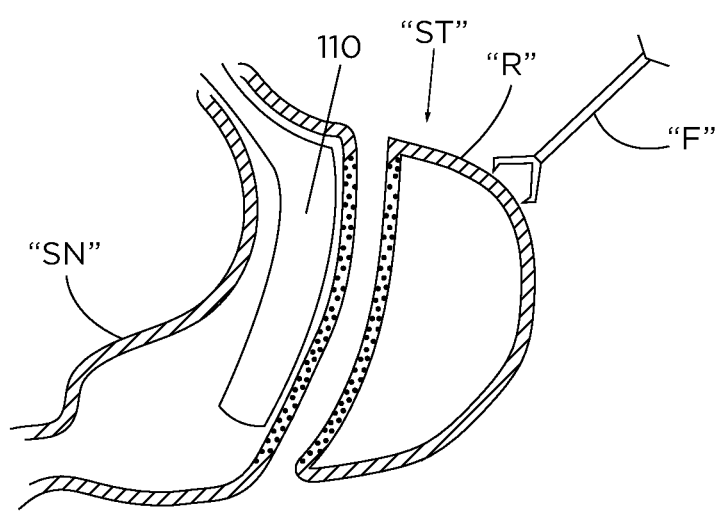
FIG. 2 is a cross sectional view of a transected stomach having the gastrectomy device of FIG. 1 disposed therein.

With additional reference to FIG. 2, once sail member 140 has been returned to the unexpanded position, transection of the stomach "ST" adjacent elongate tube 110 on an opposite side of elongate tube 110 relative to the lesser curvature portion "C1" of the stomach "ST" may be effected. In particular, one or more small incisions are created in the abdomen of the patient for receiving instruments therein to perform the transection procedure. Access ports, such as, for example, cannulae (not shown) are inserted into the small incisions made in the abdomen to maintain the small incisions open. A surgical tool, for example, a surgical stapler (not shown), is inserted into the patient through the cannula and used to transect the stomach "ST." Transecting the stomach "ST" separates the stomach "ST" into a resected portion "R" and a new stomach portion "SN." It is contemplated that any number of open or laparoscopic stomach resection techniques/devices may be used including surgical staplers, vessel sealing devices, suturing, scalpels, etc.

Transection in this manner reduces a size of the stomach "ST" (i.e., the overall internal volume of stomach "ST" is reduced from its normal, pre-transection volume) and reforms the shape of the stomach "ST" to assume a tubular configuration that generally approximates the outer dimension of elongate tube 110 and extends between the esophageal sphincter "E" and the pyloric sphincter "P." As can be appreciated, the diameter of elongate tube 110 may be selected in accordance with a desired diameter of the tubular-shape reformed stomach "ST." The resected portion "R" can be grasped by a separate forceps "F" and removed. Gastrectomy device 100 may then be removed from the stomach "ST" of patient.

With reference to FIGS. 3A and 3B, after stomach "ST" has been reduced in size by, for example, the method described above, reinforcement scaffold 200 may then be applied to the outer surface of stomach "ST." Reinforcement scaffold 200 is cut to a suitable length that approximates the circumference of the reduced size stomach "ST." In some embodiments, a plurality of variously sized reinforcement scaffolds are provided and the appropriately sized reinforcement scaffold is selected by a clinician. Reinforcement scaffold 200 is grasped by a surgical tool (not shown) and inserted into the patient through one of the cannulae. It is contemplated that an additional surgical tool is inserted through another one of the cannulae to assist in manipulating reinforcement scaffold 200 within the surgical site. A needle (not shown) having a suture (not shown) attached thereto may also be inserted laparoscopically into the surgical site.

Once reinforcement scaffold 200 is within the surgical site, to attach reinforcement scaffold 200 to stomach "ST," a first end 202a of reinforcement scaffold 200 is attached to a transection line "T" formed in stomach "ST" (i.e., the portion of stomach "ST" at which the transection was performed) via suturing. In some embodiments, first end 202a of reinforcement scaffold 200 may be attached to any portion of stomach "ST" rather than transection line "T." In some embodiments, first end 202a of reinforcement scaffold 200 may be attached to transection line "T" by a variety of fastening mechanisms other than or in addition to suturing, such as, for example, stapling, gluing, or a fastening member, for example, a toothed clip.

With first end 202a of reinforcement scaffold 200 attached to transection line "T," a second end 202b of reinforcement scaffold 200 may be wrapped around the outer surface or periphery "OS" of stomach "ST" such that reinforcement scaffold 200 forms a sleeve about the stomach "ST." Wrapping of reinforcement scaffold 200 about stomach "ST" is continued until reinforcement scaffold 200 engages and enshrouds the outer surface "OS" of stomach "ST." Second end 202b of reinforcement scaffold 200 is then attached to transection line "T" such that reinforcement scaffold 200 assumes the shape and size of the reduced size stomach "ST." In some embodiments, first and second ends 202a, 202b of reinforcement scaffold 200 overlap one another at transection line "T." It is further contemplated that reinforcement scaffold 200 may be wrapped about stomach "ST" more than once.

With reinforcement scaffold 200 wrapped about and secured to stomach "ST," reinforcement scaffold 200 resists and/or prevents stomach "ST" from dilating from the reduced size achieved during the sleeve gastrectomy procedure. As such, if the patient consumes a greater volume of food than which the reduced internal volume of stomach "ST" can hold, reinforcement scaffold 200 will substantially maintain stomach "ST" at its reduced size. In some embodiments, reinforcement scaffold 200 may be fabricated from a material having a threshold amount of pliability to allow stomach "ST" to dilate a selected amount.

With reference to FIGS. 4A and 4B, another method of reinforcing the reduced size stomach is disclosed. The method is similar to the method described above, and therefore will only be described with respect to its difference(s). The method differs from the method described above in the manner in which a reinforcement scaffold is applied to stomach "ST."

In particular, instead of applying only one reinforcement scaffold, a first reinforcement scaffold 300 and a second reinforcement scaffold 310 are provided, each being similar to reinforcement scaffold 200 described above. Reinforcement scaffolds 300, 310 are each configured to be applied to stomach "ST" after stomach "ST" has been reduced in size by a sleeve gastrectomy procedure, for example, the procedure described above.

In use, a first end 302a of first reinforcement scaffold 300 is attached to transection line "T" formed in stomach "ST." With first end 302a of first reinforcement scaffold 300 attached to transection line "T," a second end 302b of first reinforcement scaffold 300 may be wrapped around the outer surface of a first longitudinal section "A" of stomach "ST," for example, a posterior section of stomach "ST." Wrapping of first reinforcement scaffold 300 about stomach "ST" is continued until reinforcement scaffold 300 engages and enshrouds the outer surface of first longitudinal section "A" of stomach "ST." Second end 302b of first reinforcement scaffold 300 is then attached to a portion "C" of stomach "ST" that is opposite to transection line "T" such that first reinforcement scaffold 300 assumes the shape and size of the first longitudinal section "A" of stomach "ST" and adheres thereto.

With first reinforcement scaffold 300 attached to stomach "ST," second reinforcement scaffold 310 is then applied to stomach "ST." In particular, a first end 312a of second reinforcement scaffold 310 is attached to transection line "T" and a second end 312*b* of second reinforcement scaffold 310 is wrapped around the outer surface of second longitudinal section "B" of stomach "ST," for example, an anterior section of stomach "ST." Wrapping of second reinforcement scaffold 310 about stomach "ST" is continued until second reinforcement scaffold 310 engages and enshrouds the outer surface of second longitudinal section "B" of stomach "ST." Second end 312*b* of second reinforcement scaffold 310 is then attached to the portion "C" of stomach "ST" that is opposite to transection line "T" such that second reinforcement scaffold 310 assumes the shape and size of the second longitudinal section "B" of stomach "ST" and adheres thereto. As such, an entire circumference of stomach "ST" is covered by first and second reinforcement scaffolds 300, 310 to maintain stomach "ST" in its reduced size state.

It is contemplated that first ends 302*a*, 312*a* of first reinforcement scaffold or member 300 and second reinforcement scaffold or member 310, respectively, and second ends 302*b*, 312*b* of first reinforcement scaffold 300 and second reinforcement scaffold 310, respectively, may overlap one another. In some embodiments, more than two reinforcement scaffolds may be wrapped around and attached to stomach "ST" to maintain stomach "ST" in its reduced size state.

It is further contemplated that first reinforcement scaffold 300 and second reinforcement scaffold 310 may be fabricated to exhibit different physical and/or chemical characteristics from one another so that together they provide certain desirable characteristics. For example, first reinforcement scaffold 300 may be more rigid than second reinforcement scaffold 310 such that second longitudinal section "B" of stomach "ST" may be allowed to expand more than first longitudinal section "A" of stomach "ST." In some embodiments, reinforcement scaffolds 300, 310 may be cut from a roll of reinforcement scaffold.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described herein, and that various other changes and modifications may be effected by one skilled in the art without departing from the scope or spirit of the disclosure. Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

What is claimed is:

1. A system for use in a bariatric surgical procedure, comprising:
    a sleeve gastrectomy device;
    a first reinforcement scaffold sized and shaped to enshroud a first semi-circumferential portion of a stomach; and
    a second reinforcement scaffold sized and shaped to enshroud a second semi-circumferential portion of the stomach, such that the first and second reinforcement scaffolds are configured to together cover a circumference of the stomach.

2. The system according to claim 1, wherein at least one of the first or second reinforcement scaffolds is fabricated from a material that substantially resists expansion.

3. The system according to claim 1, wherein at least one of the first or second reinforcement scaffolds is selected from the group consisting of a mesh and a buttress.

4. The system according to claim 1, wherein the first reinforcement scaffold has a first longitudinally-extending side and a second longitudinally-extending side, and the second reinforcement scaffold has a first longitudinally-extending side and a second longitudinally-extending side, wherein upon coupling the first longitudinally-extending sides of the first and second reinforcement scaffolds to one another and the second longitudinally-extending sides of the first and second reinforcement scaffolds to one another, the first and second reinforcement scaffolds together from a tubular structure.

5. The system according to claim 1, wherein the first and second reinforcement scaffolds have at least one different physical characteristic from one another.

6. The system according to claim 5, wherein the first reinforcement scaffold is more rigid than the second reinforcement scaffold.

7. The system according to claim 1, wherein the first reinforcement scaffold is configured to cover a posterior section of the stomach and the second reinforcement scaffold is configured to cover an anterior section of the stomach.

8. The system according to claim 1, wherein the sleeve gastrectomy device includes a proximal end portion and a distal end portion and defines a channel between the proximal and distal end portions, the proximal end portion defining an opening therein configured to be coupled with a vacuum source.

9. The system according to claim 8, wherein the distal end portion of the sleeve gastrectomy device has a blunt tip.

10. The system according to claim 8, wherein the sleeve gastrectomy device has a series of openings defined along its length in communication with the channel.

11. The system according to claim 1, wherein the sleeve gastrectomy device includes:
    an elongate tube; and
    a sail member supported by the elongate tube and configured to move relative to the elongate tube between a contracted configuration and an expanded configuration.

\* \* \* \* \*